(12) United States Patent
Elson et al.

(10) Patent No.: US 6,692,950 B1
(45) Date of Patent: Feb. 17, 2004

(54) CLAVULANIC ACID DEHYDROGENASE, PREPARATION AND USE FOR THE PRODUCTION OF CLAVULANIC ACID

(75) Inventors: Stephen William Elson, Madrid (ES); Neville Hubert Nicholson, Dorking (GB); Stefan Roland Woroniecki, Horsham (GB); Janice Arnell, Worthing (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 08/586,664

(22) PCT Filed: Jul. 15, 1994

(86) PCT No.: PCT/EP94/02346
§ 371 (c)(1),
(2), (4) Date: Apr. 3, 1996

(87) PCT Pub. No.: WO95/03416
PCT Pub. Date: Feb. 2, 1995

(30) Foreign Application Priority Data

Jul. 24, 1993 (GB) ............................................. 9315393

(51) Int. Cl.$^7$ ........................... C12N 1/21; C12N 1/15; C12N 9/04; C07H 21/04
(52) U.S. Cl. ............................... 435/252.3; 435/254.11; 435/320.1; 536/23.2
(58) Field of Search ...................... 536/23.2; 435/320.1, 435/325, 252.3, 254.11

(56) References Cited

U.S. PATENT DOCUMENTS 4,132,712 A  1/1979  Howarth et al. ............ 540/348
4,166,904 A  9/1979  Hunt ........................... 540/348
4,556,559 A  12/1985 Cole et al. ................... 424/114

FOREIGN PATENT DOCUMENTS

| DE | 26 45 999 | 4/1977 |
| EP | 0 182 522 | 5/1986 |
| EP | 349121 | * 1/1990 |
| GB | 1 504 425 | 3/1978 |

OTHER PUBLICATIONS

Copy of EP Search Report (EP 02 07 7067, Jun. 28, 2002).

Brown, et al., "Clavulanic Acid and its Derivatives. Structure Elucidation of Clavulanic Acid and the Preparation of Dihydroclavulanic Acid, Isoclavulanic Acid, Esters and Related Oxidation Products", *Journal of the Chemical Society, Perkin Transactions 1*, pp. 635–650 (1984).

Nicholson, et al., "Evidence that the Immediate Biosynthetic Precursor of Clavulanic Acid is its N–aldehyde Analogue", *Journal of the Chemical Society, Chemical Communications* pp. 1281–1282 (1994).

Reuyl, et al., "Common Origin of Clavulanic Acid and Other Clavam Metabolites in *Streptomyces* ", *Journal of the American Chemical Society*, 114, No. 7, pp. 2762–2763 (1992).

* cited by examiner

Primary Examiner—Elizabeth Slobodyansky
(74) Attorney, Agent, or Firm—Andrea V. Lockenour; Edward R. Gimmi; Charles M. Kinzig (57) ABSTRACT

A compound of formula (I), wherein R=H or Na, or a salt thereof and an enzyme, obtainable from Streptomyces species, having clavulanic acid dehydrogenase activity which is capable of converting (I) into clavulanic acid.

5 Claims, 4 Drawing Sheets

```
AGAGGATCCC CGGGTACCGA GCTCGAATTC ACCGGGGAAT GCGACGCTGA TGATAGCGTC TGCCGTGGAC
---------+ ---------+ ---------+ ---------+ ---------+ ---------+ ---------+
GGGGAGAACT CCGGCCGCTG ATTCCCGGTG AATCCCCGGG TGTCCTCCGA AGACCATCGG AGAGCGCCGC
---------+ ---------+ ---------+ ---------+ ---------+ ---------+ ---------+
GGTATTCACC ATTCCCCGGA ACTCCCCGGG GAACTGCGGC CATCCGTACC CGGTCGGCCG TGCCCACCGC
---------+ ---------+ ---------+ ---------+ ---------+ ---------+ ---------+
AACGGTCCGG CGTACGGAAC CCGCCCCGGC ACGGCAGGTC TCACCCCTTC TTCATACGCT CACCACGATC
---------+ ---------+ ---------+ ---------+ ---------+ ---------+ ---------+
GCAGCACCAT GTGGAGGAAA TG ATG CCA TCC GCA CTC CAG GGG AAA GTC GCG CTC ATC ACG
---------+ ---------+ -- --- --- -+- --- --- --+ --- --- --- +-- --- --- -+-
                        Met Pro Ser Ala Leu Gln Gly Lys Val Ala Leu Ile Thr

GGC GCG AGC TCG GGC ATC GGC GAG GCC ACG GCC CGC GCC CTG GCC GCC GAG GGC GCC
--- --- --+ --- --- --- +-- --- --- -+- --- --- --+ --- --- --- +-- --- ---
Gly Ala Ser Ser Gly Ile Gly Glu Ala Thr Ala Arg Ala Leu Ala Ala Glu Gly Ala

GCC GTG GCC ATC GCC GCG CGC CGG GTC GAG AAG CTG CGC GCC CTG GGT GAC GAG CTG
-+- --- --- --+ --- --- --- +-- --- --- -+- --- --- --+ --- --- --- +-- ---
Ala Val Ala Ile Ala Ala Arg Arg Val Glu Lys Leu Arg Ala Leu Gly Asp Glu Leu

ACC GCC GCC GGG GCG AAG GTC CAT GTC CTC GAA CTC GAC GTC GCC GAC CGG CAG GGG
--- -+- --- --- --+ --- --- --- +-- --- --- -+- --- --- --+ --- --- --- +--
Thr Ala Ala Gly Ala Lys Val His Val Leu Glu Leu Asp Val Ala Asp Arg Gln Gly

GTG GAC GCC GCC GTC GCC TCC ACC GTC GAG GCG CTG GGC GGC CTC GAC ATC CTC GTC
--- --- -+- --- --- --+ --- --- --- +-- --- --- -+- --- --- --+ --- --- ---
Val Asp Ala Ala Val Ala Ser Thr Val Glu Ala Leu Gly Gly Leu Asp Ile Leu Val

AAC AAC GCC GGG ATC ATG CTG CTC GGC CCG GTG GAG GAC GCC GAC ACC ACC GAC TGG
+-- --- --- --+ --- --- --+ --- --- --- +-- --- --- -+- --- --- --+ --- ---
Asn Asn Ala Gly Ile Met Leu Leu Gly Pro Val Glu Asp Ala Asp Thr Thr Asp Trp

ACC CGG ATG ATC GAC ACC AAT CTC CTG GGC CTG ATG TAC ATG ACC CGG GCG GCC CTT
--- +-- --- --- -+- --- --- --+ --- --- --- +-- --- --- -+- --- --- --+ ---
Thr Arg Met Ile Asp Thr Asn Leu Leu Gly Leu Met Tyr Met Thr Arg Ala Ala Leu

CCC CAT CTG CTG CGC AGC AAG GGC ACC GTG GTG CAG ATG TCC TCG ATC GCG GGC CGG
--- --- +-- --- --- -+- --- --- --+ --- --- --- +-- --- --- -+- --- --- --+
Pro His Leu Leu Arg Ser Lys Gly Thr Val Val Gln Met Ser Ser Ile Ala Gly Arg

GTG AAC GTC CGC AAC GCG GCC GTC TAC CAG GCC ACG AAG TTC GGT GTG AAC GCG TTC
--+ --- --- +-- --- --- -+- --- --- --+ --- --- --- +-- --- --- -+- --- ---
Val Asn Val Arg Asn Ala Ala Val Tyr Gln Ala Thr Lys Phe Gly Val Asn Ala Phe

AGC GAG ACS STG CGC CAG GAG GTC ACC GAG CGC GGG GTG CGG GTC GTC GTC ATC GAG
--+ --- --- --- +-- --- --- -+- --- --- --+ --- --- --- +-- --- --- -+- ---
Ser Glu Thr Leu Arg Gln Glu Val Thr Glu Arg Gly Val Arg Val Val Val Ile Glu

CCG GGC ACC ACC GAC ACG GAG CTG CGC GGC CAC ATC ACC CAC ACC GCC ACC AAG GAG
--- --+ --- --- --- +-- --- --- -+- --- --- --+ --- --- --- +-- --- --- -+-
Pro Gly Thr Thr Asp Thr Glu Leu Arg Gly His Ile Thr His Thr Ala Thr Lys Glu

ATG TAC GAG CAG CGG ATC AGC CAG ATC CGC AAG CTC CAG GCC CAG GAC ATC GCG GAG
--- --- --+ --- --- --- +-- --- --- -+- --- --- --+ --- --- --- +-- --- ---
Met Tyr Glu Gln Arg Ile Ser Gln Ile Arg Lys Leu Gln Ala Gln Asp Ile Ala Glu

GCG GTC CGC TAC GCC GTG ACC GCG CCG CAC CAC GCG ACC GTC CAC GAG ATC T
-+- --- --- --+ --- --- --- +-- --- --- -+- --- --- --+ --- --- --- +
Ala Val Arg Tyr Ala Val Thr Ala Pro His His Ala Thr Val His Glu Ile Tyr
```

CLAVULANIC ACID DEHYDROGENASE, PREPARATION AND USE FOR THE PRODUCTION OF CLAVULANIC ACID

FIELD OF THE INVENTION

The present invention relates to a new intermediate involved in the synthesis of clavulanic acid and an enzyme useful in the synthesis of clavulanic acid from intermediates involved in its biosynthesis. The present invention also relates to processes for preparation of the enzyme and intermediate. The present invention further relates to DNA molecules carrying a gene coding for an enzyme involved in clavulanic acid biosynthesis.

BACKGROUND

The biosynthetic route to the important product clavulanic acid, a key ingredient of the antibiotic AUGMENTIN (Trade Mark of SmithKline Beecham plc) has been the subject of considerable study with a view to increasing the yield (titre) of clavulanic acid in fermentation processes. Clavulanic acid has been shown to be derived biosynthetically from clavaminic acid.

clavaminic acid      clavulanic acid

It has been reported (J. Chem. Soc., Chem. Commun. 1987, 1737 and 1990, 617) that clavaminic acid is formed by the action of an enzyme on a precursor known as proclavaminic acid (see also EP-A-0213914). Earlier steps in the biosynthetic pathway have been more difficult to elucidate.

We have now established that the final reaction in the biosynthesis of clavulanic acid involves the reduction of a side chain aldehyde to the hydroxyl group, using NADPH as the hydrogen donor.

The involvement of an aldehyde in the biosynthetic pathway has been suggested previously (Townsend et al. 1988, J Chem Soc Chem Commun, 18, 1234–36; Iwata-Reuyl, D and Townsend, C. A. 1992, J AM Chem Soc 114, 2762–4), however the present work represents the first isolation and proof of the existence of such a compound.

FIG. 1 shows the sequence of amino acids of SEQ ID No:1 in conjunction with the DNA sequence of SEQ ID NO:2 encoding same.

SUMMARY OF THE INVENTION

Accordinigly the present invention provides a compound of formula (I):

in which R is hydrogen or sodium salt thereof.

Compound (I) ("clavulanic acid aldehyde")is approximately 100 times more active as a β-lactamase inhibitor than clavulanic acid. Compound (I) has a half life of about 0.5 h in aqueous solution at 200° C. therefore it is important that it is reduced to clavulanic acid as fast as possible during biosynthesis in order to maximise the titre of clavulanic acid.

Jensen (1992) referred to a partially sequenced 11 kb fragment of DNA from S. clavuligerus at the 5th conference of the American Society of Microbiology (October 11–15, Abstract A27) and suggested that this fragment contained the complete gene complement required for the biosynthesis of a β-lactamase inhibitor assumed to be clavulanic acid. However the functions of the putative genes were not given and corresponding enzymes were not identified or isolated.

The present invention also provides an enzyme having clavulanic acid dehydrogenase (hereinafter CAD) activity which is capable of converting compound (I) into clavulanic acid under suitable conditions, in particular where compound (I) has the 2R, 5R stereochemistry.

The enzyme having CAD activity is obtainable from microorganisms especially, Streptomyces species, preferably Streptomyces clavuligerus (eg ATCC 27064), S. jumonjensis (eg ATCC 29864) or S. katsurahamanus (eg T272).

In a further aspect of the invention there is provided a method of preparing an enzyme having CAD activity by treating S. clavuligerus mycelium by centrifugation and ultrasonication followed by fractionation by ion-exchange chromatography. The enzyme is preferably in purified form, advantageously substantially pure form.

The enzyme of this invention has an apparent molecular mass of 28 kD (by SDS PAGE). It also includes the sequence of N-terminal amino acids:

1
PSALQGKVALITGASSGIGE, (SEQ ID NO:3)

In particular, the enzyme comprises the sequence of amino acids in FIG. 1 or (SEQ ID NO:1).

In a further aspect the present invention also provides DNA encoding a protein with CAD activity.

In particular the DNA comprises the DNA sequence in FIG. 1 or SEQ ID NO:2.

Figure 2:
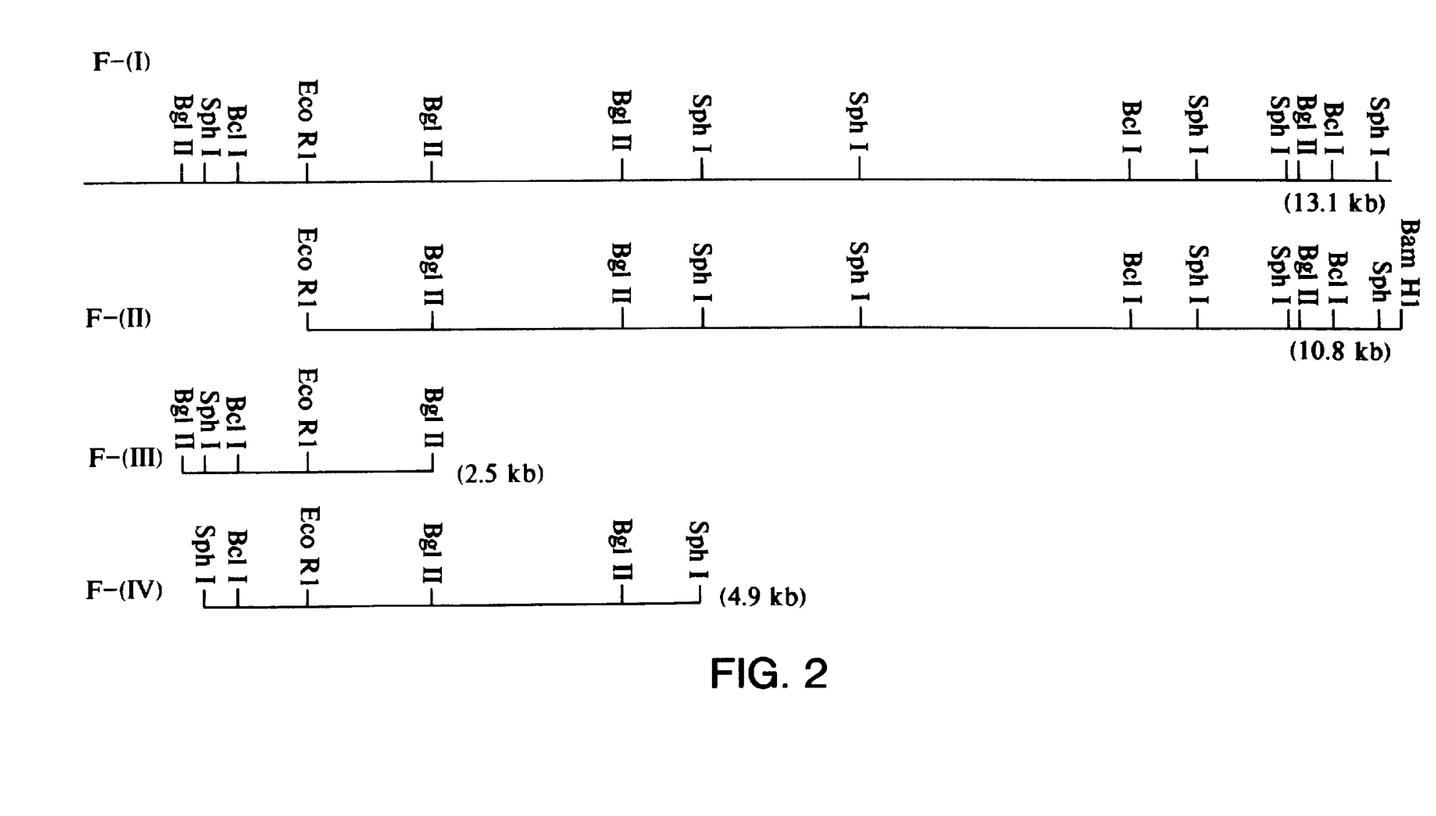
FIG. 2 shows restriction maps of DNA fragments F-(I), F-(II), F-(III) and F-(IV).

The gene encoding said protein is located within the DNA fragment (F-I) shown in FIG. 2. Fragment (F-IV) as shown in FIG. 2 is a preferred subfragment according to the invention and which contains the whole CAD gene.

The invention also provides a vector comprising such DNA, preferably an expression vector for expressing CAD in a suitable host organism. A specific example of such an expression vector is pIJ702 described by Katz., E., Thompson, C. J., Hopwood, D.A. (1983) Journal General Microbiology, 129, 2703–2714. A preferred vector is pWOR14 (FIG. 3) which is DNA fragment (F-IV) ligated to pIJ702.

DETAILED DESCRIPTION OF THE INVENTION

Figure 3:
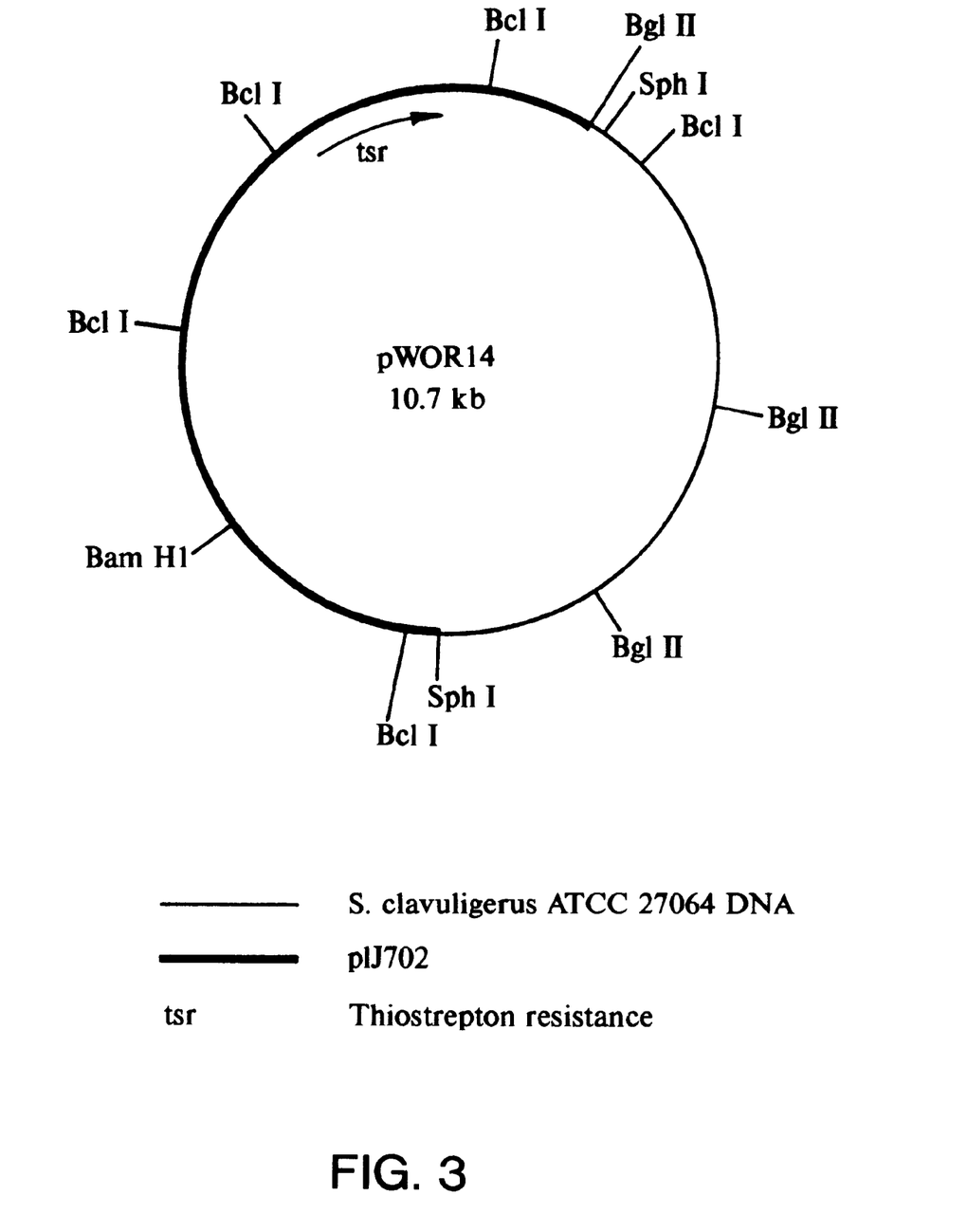
FIG. 3 is a restriction map of vector pWOR14.

In FIGS. 2 and 3 the abbreviations EcoR1, BgIII, etc are conventional abbreviations for restriction endonucleases and the approximate length in kilobases (kb) of the DNA as determined by sizing experiments carried out by agarose gel electrophoresis, is indicated. It should be understood that the Figures are not intended to show all the restriction sites present on the DNA fragments indicated.

It will be understood that the DNA of this invention is not in its natural state as it occurs in nature but is in isolated or substantially pure form.

It will be understood that the invention encompasses DNA which may not have the precise configuration of restriction sites illustrated if the said DNA has been derived by standard techniques including nucleotide deletion, substitution, addition or inversion from the DNA according to any aspect of the invention described above.

Preferably the DNA of the present invention is derived from S. clavuligerus ATCC 27064. However the invention also encompasses DNA sequences derived from other suitable organisms especially clavulanic acid producing organisms other than S. clavuligerus which sequences do not have the configuration of restriction sites shown in FIG. 2 or 3 but which hybridise, preferably under conditions of high stringency, with the DNA shown in FIG. 2 or 3 or a subfragment thereof and which code for CAD or an enzyme with CAD activity.

The DNA of the invention and vectors containing same may find use in many areas of industrial activity. That also applies to host micro-organisms transformed with said vectors and the enzymes they express. For example the DNA may be utilised as a hybridization probe to identify and isolate related or overlapping genes present on the total cellular DNA of S. clavuligerus (ATCC 27064) and of other micro-organisms which produce enzymes of similar structure and specificity. Recombinant vectors containing said DNA may be of value, when transformed into suitable hosts, in the production of genetically modified micro-organisms which synthesize increased amounts of clavulanic acid. For example, as demonstrated herein, as clavulanic acid aldehyde is relatively shortlived in vitro/in vivo, it would be very advantageous to increase the amount of activity of CAD in a suitable organism. Recombinant vectors could also be used in the generation of novel or hybrid antibiotics via the process of gene transfer (see for example D.A. Hopwood et al, Nature, 1985, 314, 642–644). Enzymes encoded by the DNA of the invention may be used, for example, in cell-free systems especially when immobilised on suitable solid supports, to prepare the known antibiotic from natural precursors or a novel antibiotic from 'unnatural' precursors obtained, for example, by chemical synthesis.

The DNA of the invention or a fragment thereof (not necessarily carrying an intact gene) may be combined, either by recombinant DNA techniques or by natural recombination processes, with a fragment of a gene involved in biosynthesis to produce a hybrid gene capable of directing the synthesis of a hybrid enzyme. Such enzymes may be used in the production of novel antibiotics by processes analogous to those hereinbefore described.

The DNA of the invention may also be modified by the known techniques of site-directed mutagenesis (in a manner analogous to that described, for example, by G. Winter et al, Nature, 1982, 299, 756–758; or by Zoller and Smith, Nucleic Acids Research, 1982, 10, 6487–6500) to give DNA in which specific mutations and/or deletions have been effected. The mutated DNA may be used to obtain an increased yield (or titre) of clavulanic acid from a suitable host micro-organism. The mutated DNA may also be used to obtain novel or hybrid antibiotics by gene transfer, or used in the production of mutant enzymes (muteins) which may be used in the production of novel antibiotics by analogous processes to those hereinabove described.

The following examples illustrate the invention.

EXAMPLE 1

Clavulanic Acid Biosynthesis: involvement of an aldehyde intermediate The aldehyde 3-oxoethylidene-7-oxo-4-oxa- 1-azabicyclo-[3.2.0] heptane-2-carboxylic acid ie compound (I) has been chemically synthesised and shown to possess $\beta$-lactamase inhibitory activity. The aldehyde can also be prepared by fermentation.

Compound (I) decomposed spontaneously in aqueous solution with a half life of one hour, but could be reduced to clavulanic acid by an NADPH dependent enzyme present in Streptomyces clavuligerus SC2. A chloroform solution of the aldehyde benzyl ester (II) was found to invert its stereochemistry spontaneously at C3 and CS at room temperature; and this result has provided a hypothetical mechanism for the inversion of stereochemistry found to occur during clavulanic acid biosynthesis. It is concluded that compound (I) occurs as a late stage intermediate in clavulanic acid biosynthesis. This pathway must include an inversion of the stereochemistry of the 3 and 5 positions of clavaminic acid. The following experiments provide evidence for the involvement of the aldehyde (I) in clavulanic acid biosynthesis.

Discussion

The aldehyde (Compound (I) was prepared as a mixture of geometric isomers about the double bond between C3 and C8 E:Z (2:1) by hydrogenolysis of the benzyl ester (If) in a yield which was estimated to be 35% by titration with sodium hydroxide solution. An h.p.l.c. assay for (I) was developed with ultra violet detection of the allylic aldehyde chromophore at 260nm. Fractions of the h.p.l.c. eluent which contained the chromophore were evaporated to dryness and shown to contain (I) by nmr spectroscopy. Repeated h.p.l.c. analysis of a solution of the salt (III) showed that, at room temperature, about half had decomposed in one hour. This instability prevented full characterisation of the acid (I), so it was converted with diazomethane to its methyl ester (IV) in an overall yield of 16% from the benzyl ester (II) (A.G. Brown et al, J. Chem. Soc. Perkin Trans. I, 1984, 635). The spectral data obtained for the methyl ester (IV) were indistinguishable from those obtained by A. G. Brown et al 1984.

Compound (I) was reduced to clavulanic acid by NADPH in the presence of a broken cell suspension of S. clavuligerus SC2 (Table 1). (SC2 is a reisolate of ATCC 27064). The clavulanic acid produced was detected by KaG bioassay (AG. Brown et al J. Antibiot., 1976, 29, 668) and chromatographic tapes loaded with the reaction mixture, were compared with standards to confirm the presence of clavulanic acid. The reduction was complete before a sample could be removed from the reaction vessel, but appeared to give clavulanic acid in only 14% yield. However, should the enzyme be capable of reducing only the Z isomer of (I) (the geometry of clavulanic acid), the yield is 42%. The failure of the reduction when NADH was used in place of NADPH and when the broken cell suspension was absent or boiled, indicates that the reaction is catalysed by an NADPH dependent enzyme or enzymes present in the broken cell suspension.

TABLE 1

Reduction of (III) by a broken cell suspension (BCS) of *S.clavuligerus* SC2

| Reaction Mixture | Clavulanic Acid (μg/ml) at time | |
|---|---|---|
| | 0 mins (KaG bioassy) | 60 mins |
| BCS' + (III) | 8.0 | 7.0 |
| BCS' + (III) + NADPH | 28.8 | 27.2 |
| BCS' + NADPH | 2.4 | 2.4 |
| (III) + NADPH | 8.8 | 7.2 |
| Boiled BCS' + (III) + NADPH | 6.6 | 6.6 |
| BCS' + (III) + NADH | 6.2 | 6.6 |

'BCS is broken cell suspension (Woroniecki et al. U.S. Pat. No. 4,795,809 ex 21).

The concentration of NADH or NADPH above is 1 mM.

While the above demonstrates that *S. clavuligerus* can reduce (I) to clavulanic acid, it offers no explanation of the inversion of stereochemistry at the 2 and 5 positions during the biosynthesis of clavulanic acid. Certain authors have proposed theoretical schemes for this phenomenon [Recent Advances in the Chemistry of β-lactam antibiotics, G. I. Gregory, ed, 2nd International Symposium, Royal Soc. Chem (No 38) p158]. However, we have found that when the aldehyde benzyl ester (II) in chloroform solution was examined by nmr using enantioselective solvating reagent, and by optical rotation, it was found to racemise its stereochemistry at the two and five positions (scheme shown below) spontaneously at room temperature. An ester of the aldehyde might, therefore, be the biosynthetic intermediate at which the clavaminic acid stereochemistry is inverted to the clavulanic acid stereochemistry.

Scheme

Experimental

Preparation of Sodium 3-Oxoethylidene-7-oxo-4-oxa-1-azabicyclo (3.2.0)heptane-2-carboxylate (III)

Benzyl 3-oxoethylidene-7-oxo-4-oxa-1-azabicyclo[3.2.0] heptane-2-carboxylate (II) (50 mg, 0. 17m mol) was dissolved in tetrahydrofuran (5 ml) and 0.2 M sodium phosphate adjusted to pH 6.85 (5 ml), and hydrogenated at ambient temperature and pressure for ten minutes with 10% palladium on carbon (40 mg). The reaction mixture was rapidly filtered and evaporated to dryness while the temperature was maintained below 10° C. The residue was immediately redissolved in $D_2O$ to give a solution of the title compound (III). $\delta_H$(250 MHz, $D_2O$) inter alia E isomer 3.25 (1H, d, J 17.4 Hz, 6β-H), 3.65 (1H, dd, J 17.4 and 2.9 Hz, 6 α-H), 5.73 (1H, d, J 1.2 Hz, 2-H), 5.79 (1H, dd, J 8.3 and 1 Hz, 8-H), 5.94 (1H, d, 2.7 Hz, 5-H), 9.55 (1H, d, J 8.3 Hz, 9-H), Z isomer 3.29 (1H, d, J 17.3 Hz, 6β-H), 3.65 (1H, dd, J 17.4 and 2.9 Hz, 6 α-H), 5.27 (1H, s, 2-H), 5.50 (1H, d, J 8.2 Hz, 8-H), 6.00 (1H, d, J2.7 Hz, 5-H), and 9.70 (1H, d, J 8.2 Hz, 9-H). The E and Z isomers were assigned on the relative positions of their 8-proton resonance (Gerald Brooks+Eric Huit J.Chem.Soc. Perkin Trans. I (1983) 2513) and were in the ratio E-Z (2:1). Material prepared by the above hydrogenation with water substituting for the phosphate solution and adjustment of the pH of the reaction mixture to 6.5 with 0.1 M NaOH gave (III) (Yield 35% from NaOH consumed), λmax. ($H_2O$) 262 nm; vmax.(KBr) 3 400, 1 792 (br), and 1 640 $cm^{-1}$ (br), and 1 640 $cm^{-1}$ (br); thin layer chromatography on silica 60 eluted with butan-1-ol-ethanol-water (4:1:1) and visualised with Schiffs reagent gave a blue zone (Rf:0.52). Addition of a known weight of fumaric acid to the crude product solution followed by evaporation and nmr analysis indicated a yield of 20% by comparison of the intensity of the fumarate protons with the intensity of the aldehydic proton of (M). When this solution was allowed to stand at room temperature for 3.5 hours, (III) was seen to have decomposed to a yield of 3.2%.

β-lactamase inhibition by (III): A solution of III was tested as a β-lactamase inhibitor by the automated chromogenic substrate assay of C. Reading and T. Farmeragainst Klebsiella E70 β-lactamase. Taking the yield of (III) from the hydrogenation reaction as 35% gave an $I^{50}$ with pre-incubation of 0.01 μg/ml and without pre-incubation of enzyme and inhibitor of 1μg/ml.

HPLC of (I)

Analytical: A Waters $C_{18}$ Microbondapak column was eluted at 2 mls/min with 0.1 M sodium phosphate at pH 3.2. The eluent was monitored by an ultra violet detector at 260nm. The retention time of (I) was 5.6 minutes.

Preparative: Half of the (III) prepared by hydrogenation was evaporated to a small volume, adjusted to pH 4.0 with 0.5M orthophosphoric acid and made up to 2 ml with water. This solution was chromatographed over a Waters $C_{18}$ Radpak cartridge supported in a Waters Z module and elected at 4 mls/min. with 0.1M sodium phosphate adjusted to pH 4.0. A fraction coincident with the elution of a strong chromophore at 260nm was collected between 3.8 and 5.0 minutes. Evaporation of this fraction followed immediately by nmr gave a spectrum consistent with (III).

Spontaneous decomposition of.(III):- A solution of (5) in 0.2 M aqueous sodium phosphate at pH 6.85 was allowed to stand at room temperature. h.p.l.c. analysis showed the solution to contain 85% of the original (III) after 35 minutes and 63% after 53 minutes.

Methyl 3-oxoethylidene-7-oxo4oxa-1-azabicyclo[3.2.0] heptane-2-carboxylate (IV):- Benzyl 3-oxoethylidene-7-oxo 4 oxa-1-azabicyclo[3.2.0]heptane-2-carboxylate (II) (100 mg, 0.35 ml) was hydrogenolysed as before to provide (I) in water (10 ml). This solution was acidified to pH 2.5 under a layer of ether (5 ml) at 4° C. and stirred for five minutes with each of three aliquots of diazomethane. After twenty minutes, excess diazomethane was removed by a stream of nitrogen and ethyl acetate (30 ml) was added. The organic layer was separated, dried with magnesium sulphate and chromatographed rapidly over silica gel in ethyl acetate - hexane (1:1)) to give the title compound as mixture of geometric isomers E-Z (1.8:1) (12 mg, 16% from the ester (II)). The spectral data obtained for these isomers were indistinguishable from those obtained from the previous preparation.

Enzymic reduction of (III) to clavulanic acid:- solution of (III) (0.23 mg, 1 μmol, estimated by titration of acid (I)) in water (0 ml 1μmol) was added to washed 48 hour *S.clavuligerus* SC2 cells which had been sonicated (EP 0213 914 example 20) (0.5 ml). The suspension was treated with 10 mM NADPH (0.1 ml, 1 umol), made up to one milliliter with 50 mM MOPS buffer at pH 7.0 and incubated in stoppered tubes at 26° C. Samples (0.2 ml) were removed, treated with methanol (0.2 ml) for 5 minutes, and centrifuged. The clear supernatants were made up to 1.6 ml with MOPS buffer and assayed on discs by the KaG method. Undiluted reaction mixture was applied to Whatman No. 1 chromatography tapes which were developed in either butan-1-ol-acetic acid-water (12:3:5) or butan-1-01-ethanol-water (7:1:2), dried, and visualised by application to a KaG bioassay plate. Standard clavulanic acid solutions were developed and visualised similarly.

Racemisation of benzyl 3-oxoethylidene-7-oxo4-oxa-1-azabicyclo[3.2.0] heptane-2-carboxylate (II):- A solution of the title compound (II) as a mixture of geometrical isomers E-Z (2:1) (162 mg, 0.56mmol) in chloroform (8 ml) was allowed to stand at ambient temperature away from strong light for three days. The solution was evaporated to dryness, chromatographed over silica gel in ethyl acetate-hexane (1:1), and, on evaporation, gave the title compound in the ratio of geometric isomers E-Z (1.7:1) (53 mg, 33%), $[\alpha]^{20}$+16.4° (c=2% in dichloromethane); addition of R-2,2,2-trifluoro-1-(9-anthryl)ethanol (1000% by weight) to the nmr solution (250 MHz, CDCl$_3$) caused two sets of signals to appear for the 6b, 6a and 8 protons of both the E and Z isomers and for the 2 proton of the E isomer. Irradiation of specific protons demonstrated coupling between the 5 and 6 and the 8 and 9 protons for all these signals. The intensity of the signals indicated a 65:35 mixture of enantiomers. When the title compound was freshly prepared the geometric isomer ratio was E-Z (1.6:1), $[\alpha]^{20}$+53.9° (c=2% in dichloromethane); and addition of R-2,2,2 trifluro- 1-(9-antreyl)ethanol to the nmr solution showed a 93:7 mixture of enantiomers.

Conclusion

The presence of an enzyme in a clavulanic acid producing strain of *S.clavuligerus* which can reduce (I) to clavulanic acid suggests that (I) is a naturally occurring anabolite. The enantiomeric exchange demonstrated by the ester (II) can explain the inversion of stereochemistry which occurs during the biosynthesis of clavulanic acid from clavaminic acid but provides no proof that such a mechanism applies in vivo. Confirmation that compound (I) is a biosynthetic intermediate and that these mechanisms are operating, has been confirmed by the discovery of compound (I) naturally occurring in *S. clavuligerus* broth.

EXAMPLE 2

Stereochemistry and Biosynthesis Experiments

Naturally occurring 3-oxoethylidene-7-oxo-4-oxa-1-azabicyclo[3.2.0]heptane-2-carboxylic acid (I) has been identified by h.p.l.c. at a concentration of circa 0.4μg/ml in the broth of the clavulanic acid producing Streptomyces. clavuligerus SC2 and circa 4 μg/ml in the broth of the clavulanic acid deficient mutant *S. clavuligerus* dcl I 111. (The *S. clavuligerus* mutant Dcl I 111 was isolated during random screening procedures for high titre clavulanic acid producing mutants). A decarboxylated derivative (V) was isolated from the latter broth and shown to possess 5-R stereochemistry.

Fresh dcl I 111 broth gave strong β-lactamase inhibitory activity which decayed at the same rate as chemically synthesised 2R,5R-(1). The last two results indicate that the stereochemistry of naturally occurring (I) is 5R—the same as that of clavulanic acid; and it is therefore concluded that (I) is the immediate biosynthetic precursor to clavulanic acid.

Naturally occurring (I) was identified by h.p.l.c. in the clavulanic acid deficient mutant *S. clavuligerus* dcl I 111. These organisms were fermented for between 43 and 60 hours when their broth supernatants were extracted with methyl acetate at acidic pH. The extracts were concentrated and shown to possess an h.p.l.c. peak which had the same retention time and ultra violet absorption spectrum as (I) chemically synthesised from clavulanic acid. Quantitation of (I) is difficult due to its chemical instability, but approximation was made by comparison of the intensity of the broth derived h.p.l.c. peak either with that of synthetic (I), or with that of a more stable derivative possessing a similar chromophore. Comparison with synthetic (I) give a broth concentration for *S. clavuligerus* dcl I 111 of 4μg/ml (I). Comparison with the h.p.l.c. peak of a solution of (V) of known concentration gave broth concentrations of (I) of half these values.

(V)

Isolation of (I) from I 111 broth is prevented by its chemical instability. However, synthetic (I) decarboxylates in good yield to give the derivative (V) with retention of stereochemistry at the 5 position. The derivative (V) is chemically and stereochemically stable in organic solution and survives rapid silica chromatography (recovery 70%). It is therefore suitable for isolation, characterisation and stereochemical evaluation and this data will indirectly provide the corresponding data for naturally occurring (I). For these reasons (I) in I 111 broth was converted by decarboxylation to the derivative (V).

The methyl acetate extract (MAE) of dcl I 111 was allowed to stand at room temperature and the formation of the decarboxylated derivative (V) from natural (I) was monitored by h.p.l.c. The E isomer of (V) so formed was purified by chromatography over Sephadex LH 20 and high pressure semi-preparative silica chromatography. The nmr, ir, uv, h.p.l.c. and mass spectral data for this compound were indistinguishable from those for a sample of E-V chemically prepared from clavulanic acid. However, when enantiomeric solvating reagent (esr) was added to the nmr solution of the synthetic material, the doublet of doublets due to the 2βproton was split into two sets of signals in the ratio 2:1. When E-V from natural sources was treated in the same way, only one set of 2βproton signals could be observed. These results indicate that the synthetic-material was a mixture of enantiomers at the 5 position, while the naturally derived E-V was a single enantiomer. The enantiomeric purity of the natural material demonstrates that only a single isomer of (I) exists in vivo and that the 5 position of this molecule does not undergo racemisation either in (I) itself or when that molecule decarboxylates. The synthetic E-V was a mixture of enantiomers due to the previously reported racemisation of the benzyl ester (II) from which it was made; and, since the ester (II) was prepared from 2R, 5R clavulanic acid, the major isomer in synthetic E-V must be 5R. In order to determine the absolute stereochemistry of the naturally derived E-V, the solution of this material which had been treated with esr was added to the similarly treated solution of synthetic E-V. N.mr. spectroscopy showed that the intensity of the major set of 6β proton signals had increased relative to the minor. Naturally occurring (I) must, therefore, possess the 5R stereochemistry.

Circular dichroism spectroscopy provides corroboration for these conclusions. The decarboxylated products E-V share the same chromophore and a positive Δε, but the intensity of the absorbtion of the natural material is 2.4 times that of the synthetic material. Thus, natural E-V has the 5R stereochemistry and must be derived from (I) with 5R stereochemistry.

Figure 4:
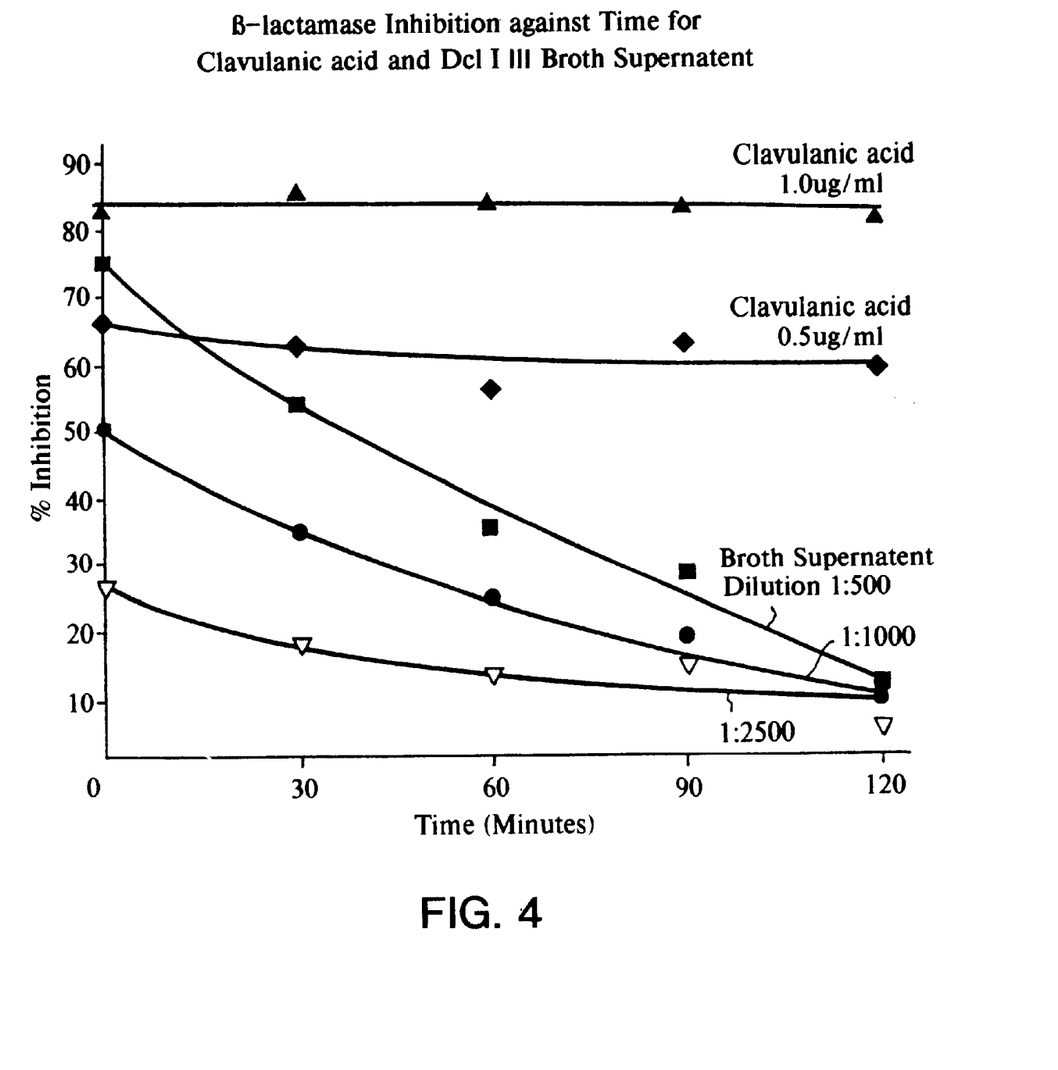
FIG. 4 is a graphical representation of beta-lactamase inhibition in the experiments of Example 2.

Both the presence and stereochemistry of (I) in dcl I 111 may be inferred from the β-lactamase inhibitory activity of the broth supernatant. Fresh samples of 45 hours I 111 supernatant were tested by the chromogenic cephalosporin assay Antibiotic: Assessment of antimicrobial activity and resistance( A. Denver Russell and Louis B (eds). Quesxel—page 147.) and shown to possess β-lactamase inhibitory activity against R TEM JT4 equivalent to that of a solution of 375 mg/ml of clavulanic acid. Unlike the clavulanic acid solution, the activity of the broth supernatant decayed with an approximate half life of one hour at room temperature (FIG. 4). Strong β-lactamase activity and the same rate of decomposition were found in (I) chemically synthesised from 2R, 5R clavulanic acid, so similar transient β-lactamase inhibitory activity in I 111 broth may be attributed to the presence of (I). Previous publications (S. W. Elson, J. Gillett, N. H. Nicholson, and J. W. Tyler, J. Chem. Soc. Chem. Commun. 1988 979; S. W. Elson, K.H. Baggaley, J. Gillett, S. Holland, N. H. Nicholson, J. T. Sime, and S R. Woroniecki, J. Chem. Soc. Chem Commun. (1987) 1937) have shown that, although clavulanates with the 2R, 5R stereochemistry possess strong β-lactamase inhibitory activity, those possessing the 2S,5S stereochemistry do not. This activity therefore, is consistent with 2R, 5R stereochemistry for the (I) in dcl I 111 broth.

In summary, the presence of (I) in S. clavuligerus broth has been demonstrated by h.p.l.c. and ultra-violet spectroscopic comparison with a synthetic standard, by its β-lactanase inhibitory activity and by isolation and characterisation of a decarboxylated derivative. The stereochemistry of natural (I) was confirmed as 5-R by its β-lactamase inhibitory activity and by comparison of the decarboxylated derivative with the same compound of known stereochemistry.

Conclusion

SC2 has been shown to possess an NADPH dependent enzyme capable of reducing (I) to clavulanic acid. Here, we have shown that the clavulanic acid deficient mutant dcl I 111 accumulates (I) to a steady state concentration, determined by its rate of production and decomposition, which is ten fold higher that the concentration found in SC2. From these results we deduce that I 111 is unable to produce clavulanic acid because of a deficiency in the enzyme performing the reduction and that (I) is, therefore, on the biosynthetic pathway to clavulanic acid. Since (I) and clavulanic acid share the 5-R stereochemistry we conclude that (I) is the immediate biosynthetic precursor to clavulanic acid.

Extraction of (I) from S. clavuligerus broth:

S. clavuligerus dcl I 111 was fermented essentially as in European patent 0213 914 example 20. At 50 hours, the broth was rapidly cooled to 2° C. The methyl acetate extract (MAE) was maintained at less than 10° C. and was used immediately in the following experiments.

H.p.l.c. assay for (D in S. clavuligerus broth:- A sample of the methyl acetate extract (MAE) (10 ml) was evaporated to an aqueous residue, readjusted to pH 3.2 and made up to a known volume of about 0.5 ml. This sample was immediately compared with a fresh, chemically prepared sample of (I) by h.p.l.c. (conditions analytical) and gave a peak equivalent to 4μg/ml of (I) for the I 111 culture broth. A similar assay using broth S. clavuligerus SC2 gave a broth concentration of 0.4 μg/ml (I).

Hplc Conditions

B (for derivative (V)): Waters Microporasil Radpak column supported by RCM 8×10 and eluted at 2 mls/min with chloroform-hexane-ethanol (3:6:0.1). Ultra-violet detection at 255 nm using a diode array monitor. V—retention time 6.0 minutes; λmax 255 nm; 2.5μg gives an absorbtion of 0.25 OD.

C (for derivative (V)): As B eluting with dichloromethane hexane-ethanol (3:6:0.1).

Purification of 5R-E-3-oxoethylidene-7-oxo-4-oxa-1-azabicyclo[3.2.0]heptane (E-V) from S. clavuligerus dcl I 111 broth; The methyl acetate extract (MAE) (1.15 liters) was allowed to stand at room temperature for four hours when h.p.l.c. (conditions B) showed no further increase in the peaks due to the decarboxylated product.

The solution was then evaporated to a small volume, the residue diluted with chloroform (200 ml) and the resulting aqueous phase (50 ml) discarded. The organic phase was washed with 1M sodium phosphate solution at pH 6.5, dried with magnesium sulphate and evaporated to dryness. This residue was chromatographed over Sephadex LH 20 in ethyl acetate-hexane (1:1) to give an oil (40 mg oil containing 2.0 mg (E-V); purity 5.0%). Material prepared in this fashion (30 mg) was chromatographed repeatedly (conditions B followed by C) and gave 5R-E-3-oxoethylidene-7-oxo-4-oxa-1-azabicyclo[3.2.0]heptane (0.8 mg); CDA $\Delta E_{237.4}$ 14.6 ($CH_3CN$); (Found $M^+$153.0438. Calc. for $C_7H_7NO_3$: $M^+$153.0426); λmax.($CH_3CN$) 249 nm (ε4, 187 $dm^3$ $mol^{-1}$ $cm^{-1}$); Vmax.(KBr) 1 797, 1 668, 1 637, and 1 592 $cm^{-1}$; $\delta_H$ (250 MHz, $CDCl_3$) 3.12 1H, d, J 16.7 Hz, 6β-H), 3.54 (1H, ddd, J 0.9, 2.8 and 16.6 Hz, 6α-H), 3.92 (1H, d, J17.5 Hz, 2α-H), 5.01 (1H, dd, J1.6 and 17.5 Hz, 2β-H), 5.66 (1H, d, J 2.7 Hz, 5-H), 5.82 (1H, ddd, J 1.7, 1.7 and 3.6 Hz, 8-H) and 9.50 (1H, J 4.9 $H_3$, 9-H). Irradiation of the 8-H signal caused a collapse of coupling at the 9-H signal, loss of the smaller coupling at the 20β-H and sharpening of the 2α-H signal. Irradiation of the 2α-H signal caused loss of the smallest coupling at 6α-H. Addition of R-2,2,2-trifluoro-1-(9-anthyl) ethanol (1000%) caused no bifurcation of the signal due to the 2β proton. Addition of the latter nmr solution to a solution demonstrating a 2:1 (R:S) mixture of enantiomers, showed a relative reduction in the intensity of the 2β proton of the 5-enantiomer m/z 153 ($M^+$, 9%), 136 (impurity, 15.3%), 125 ($M^+$—CO, 6.3%), 111 ($M^+$—$CH_2CO$, 18.9%, 55 (100%).

Preparation of 3-oxoethylidene-7-oxo-4-oxa-1-azabicyclo [3.2.0] heptane (V) from synthetic (I):- A solution of (D) (21.6 mg, 11 mol) prepared by hydrogenation of benzyl 3-oxoethylidene-7-oxo-4-oxa-1-azabicyclo[3.2.0] heptane-2-carboxylate (II) (90 mg, 0.31 mmol) in tetrahydrofuran (90 ml) was allowed to stand at room temperature for four hours when h.p.l.c. (conditions B) showed no further increase in the signal due to (E-V). The reaction mixture was evaporated to dryness and redissolved in ethyl acetate (50 ml). The ethyl acetate solution was washed with saturated NaHCO$_3$, 0.1M HCl and saturated NaCl, dried with magnesium sulphate, and evaporated to an oil (50 mg). Semi-preparative h.p.l.c. of this residue (conditions C) gave E-3-oxoethylidene-7-oxo-4-oxa- 1 -azabicyclo[3.2.0] heptane (8.3 mg, 49%) CD $\Delta\epsilon_{237.4}$ 6.1 CH$_3$CN); $\lambda$.max. (CH$_3$CN) 249 nm ($\epsilon$l3,399 dm$^3$ mol$^{-1}$ cm$^{-1}$); Vmax. 1 794, 1 669, 1 638, and 1 591 cm$^{-1}$; $\delta_H$(250 MHz, CDCl$_3$) 3.19 (1H, d, J 16.7 Hz, 6$\beta$-H), 3.59 (1H, ddd, J 0.9, 2.8 and 16.6 Hz, 6$\alpha$-H), 3.99 (1H, d, J 17.5 Hz, 2$\alpha$-H), 5.06 (1H, dd, J 1.5 and 17.4 Hz 2$\beta$-H), 5.72 (1H, d, J 2.8 Hz, 5-H), 5.87 (1H, ddd, J 1.7, 1.7 and 3.5 Hz, 8-H) and 9.57 (1H, d, J 5.0 Hz, 9-H); addition of R-2,2,2-trifiuoro-1-(9-anthryl)ethanol (1000%) caused separation of the signals due to the 2$\beta$ proton chemical shift caused both sets of 2$\beta$ protons to loose their smaller coupling. The two sets of 2$\beta$ proton signals were in the ratio 2:1 m/z 153 (M$^+$, 23%), 125 (M$^+$-CO, 12%), 111 (M$^+$CH$_2$CO, 24%) and 55 (M$^+$-98, 100%). Further elution gave Z-3-oxoethylidene-7-oxo-4-oxa-1-azabicyclo[3.2.0]heptane containing 5% of the E isomer (2.3 mg, 14%), Vmax. 1 792 and 1 660 c$^{-1}$ (br); dH (250 MHz, CDCl$_3$) 3.25 (1H, d, J 16.8, 6$b$-H), 3.52 (1H, ddd, J 0.8, 2.8 and 16.9 Hz, 6$\alpha$-H), 3.85 (1H, d, J 16.8 Hz, 2$\alpha$-H), 4.68 (1H, dd, J 0.8 and 17.0 Hz, 2$\beta$-H), 5.23 (1H, dt, J 1.0 and 7.9 Hz, 8-H), and 9.96 (1H, d, J 7.8 Hz); m/z 153 (M$^+$24%) 125 (M$^+$CO, 11%) 111, (M$^+$CH$_2$CO, 29%), and 55 (M$^+$-98, 100%).

$\beta$-lactamase inhibition by dcl I 111 supernatant:- The $\beta$-lactamase inhibitory activity of dcl I 111 supernatant was estimated by the chromogenic cephalosporin assay of Reading and Farmer. A solution of nitrocephin (250 mg/ml) and RTEM JT4 $\beta$-lactamase from *E. coli* (5×10$^{-3}$ BCD) in 0.05 M sodium phosphate at pH 7.3 was incubated at 37° C. The optical absorbtion of this reaction mixture at 492 nm was read in a 1 cm cuvette every minute for nine minutes to obtain an initial rate $\beta$-lactamase activity. Standard reactions containing aliquots of a solution of clavulanic acid (final concentrations: 1.0 and 0.5 mg/ml) in phosphate buffer were assayed in the same manner. Test reactions contained 43 hour dcl I 111 supernatant at known final dilutions. The clavulanic acid stock solution and the dcl I 111 supernatant were allowed to stand at room temperature, and were assayed for their initial rate of $\beta$-lactamase activity every half hour (see FIG. 4).

EXAMPLE 3

A One-step Purification of Clavulanic Acid Dehydrogenase (CAD) from *Streptomyces clavuligerus* SC2

SC2 is a reisolate of ATCC 27064. SC2 cells were grown in the standard carbohydrate medium (Woroniecki et al U.S. Pat. No. 4,795,809), harvested by centrifugation and then sonicated in the following buffer:

50 mM MOPS
10% v/v glycerol
1 mM dithiothreitol (DTT)
1 mM ethylene diamine tetraacetic acid (EDTA)
1 mM phenylmethylsulphonyl fluoride (PMSF)
1 mM benzamidine-HCI
10 $\mu$M L-trans-epoxysuccinyl-leucylamido (4-guanidino) butane
pH7.5

The cocktail of protease inhibitors was found to be necessary after loss of activity was observed on initial purification attempts.

Cell debris was removed by centrifugation and then the sonicate was made up to 1% streptomycin sulphate and left at 4° C. for 30 minutes. After this time the nucleic acid precipitate was removed by centrifugation and the remaining supernatant loaded onto the column.

The resin used was Red-Sepharose (Pharmacia), a dye resin known to have particular affinity for NADPH-dependent dehydrogenases (Pharmacia booklet, Affinity Chromatography, Principles and Methods). A 10 ml column was equilibrated in the above buffer and then 10 ml of treated sonicate was loaded on over one hour. After extensive washing with buffer, the column was pre-eluted with 10 ml of 10 mM NADH (to remove non-NADPH-dependent enzymes). Once the A$_{280}$ reading of the eluate had returned to baseline levels after washing with buffer, the column was eluted with an 8 hour linear gradient of NADPH (0–10 mM) in buffer, at 10 ml/hr. Ten minute fractions were collected and assayed for CAD activity. The assay for CAD is based on the well-known 'KAG' assay for $\beta$-lactamase inhibitors.

3.1 Assay

*Klebsiella pneumoniae*, NCTC 11228, is grown on DST agar containing 5 $\mu$g ml$^{-1}$ penicillin G, with assay samples being placed in 8 mm wells. The samples are prepared by incubating the following:

25 $\mu$l column fraction
40 $\mu$l buffer (as above)
10 $\mu$l NADPH (10 mM)
25 $\mu$l clavulanic acid aldehyde (1 mg/ml approx)

at 21° C. for 10 minutes, before stopping the reaction with 300 $\mu$l cold buffer and adding 90 $\mu$l to the plate wells. In order to eliminate false results (due to non-enzymic effects/presence of clavulanic acid, etc.) each sample is also assayed in the absence of NADPH. After overnight incubation at 37° C., the zones of inhibition (due to clavulanate production) are measured. A small zone is observed even in the absence of CAD, due to residual aldehyde which is inhibitually active in its own right or other $\beta$-lactamase inhibitor (eg. clavulanic acid).

N.B. The aldehyde of clavulanic acid is very unstable (half-life about 30 minutes at 21° C.) and must be prepared fresh within one hour of anticipated use and kept on ice.

3.2 Characterisation

Protein with CAD activity was found to elute at 1–2 mM NADPH. (NB. Absorbance readings at 280nm are not useful indicators of protein elution due to the absorbance of NADPH at this wavelength, therefore assays are required.) An SDS-PAGE analysis of the active fraction showed three bands - a prominent band at 28 kD and a fainter doublet at 26kD. The gel was Western blotted onto an Immobilon-P membrane (Millipore). N-terminal amino acid sequencing analysis showed that all three protein bands shared the same N-terminal sequence:

1
PSALQGKVALITGASSGIGE(SEQ ID NO:3
deduced fromgene (M) PSALQGKVALITGASSGIGE
SEQ ID NO:3

EXAMPLE 4

Identification of the CAD gene 4.1 Preparation of an *S. clavuligerus* mutant (Dcl I 111) Blocked in Clavulanic Acid Biosynthesis The *S. clavuligerus* mutant Dcl I 111 was isolated during, random screening procedures for high titre clavulanic acid producing mutants. The mutant accumulates clavulanic acid aldehyde.

4.2 Complementation of the Lesion in DclI III by Clones pBROC42 and pBROC41 and PWOR14 a. Preparation of pBROC41

Vector pBROC41 was constructed by ligating the BamnH1/EcoR1 fragment F-II in FIG. 2 from DNA fragment F-I in FIG. 2 (derivation described in EP 0 349 121) into pIJ913 described by Hopwood et al (1985) Genetic Manipulation of Streptomyces , A Laboratory Manual. The John Innes Foundation.

b Preparation of pBROC42

Vector pBROC 42 was constructed by ligating a 2.5kb BgIII fragment (F-III in FIG. 2) from DNA fragment F-I (FIG. 2) (for derivation see EP 0 349 121) into pIJ702 described by Katz, E., Thompson, C. J., Hopwood, D.A. (1983) Journal General Microbiology 129, 2703–2714.

c Preparation of pWOR14

Vector pWOR14 (see FIG. 3) was constructed by ligating the 4.9kb Sphl fragment F-IV in FIG. 2 from DNA fragment F-I in FIG. 2 (for derivation see EP 0 349 121) into pIJ702 described by Katz, E., Thompson, C. J., Hopwood, D. A. (1983) Journal General Microbiology 129, 2703–2714.

d Complementation of Mutant dclI 111

Vectors pBROC 41, pBROC 42 and pWOR14 were used to transform the dclI 111 as described in Bailey, C.R. et al Biotechnology 2, 808–811 (1984) and thiostrepton resistant transformants were streaked onto M5D plus thiostrepton at % ug/ml (EP 0349 121).

Transformants of dclI 111 with pBROC41, pBROC42 and pWOR14 were tested for the repair of clavulanic acid by means of a plate bioassay. Cells of each transformant were stabbed onto M5D and incubated at 26 C for 6 days. The bioassay plates were then overpoured with soft blood agar (Oxoid) containing a strain of Klebsiella aerogenes described in Reading, C. and Cole, M. (1977) Antimicrob. Agents Chemorther. 11, 852–7, 0.02% terazolium salts and 5 µg/ml penicillin G. After overnight incubation at 26 C zones of inhibition had formed around the transformed colonies which were greater than those around the untransformed control (essentially zero).

Transformants containing pBROC41 and pBROC42 giving zones showing greater than the control culture were transferred to shake flask culture for accurate titre assessment. Cells from each colony were inoculated into 20 ml of seed medium (EP 0 349 121) with the addition of thiostrepton (5 µg/ml final concentration) and grown for 3 days at 26° C. with shaking. 1 ml of the seed culture was then inoculated into a final stage medium (EP 349 121) containing 5 µg/ml thiostrepton and grown at 260° C. for up to four days. Samples of the final stage broth were withdrawn after three or four days growth and assayed for clavulanic acid productivity as described in Bird, A.E. et al (1982) Analyst 1071241–1245 and Foulstone, M. and Reading, C. Antimicrob. Agents Chemother., 22,753–762.

Results: Clavulanic acid was produced in pBROC42 transformants of dclI 111 to 50% of the producing grandparent, and pBROC41 transformants to 15% of the producing grandparent The grandparent strain is the producing parent of dclI 11. It was concluded that the DNA inserts II and III contain the gene for which there is a mutation in dclI 111.

Conclusion: CAD lies wholly within pBROC 41. It was concluded that pBROC41, pBROC42 and pWOR14 contain inserts complementing the dclI 111 mutation in the CAD gene.

4.3. Sequencing of Clone pMG42

FIG. 2 shows a restriction map of part of the clavulanic acid gene cluster. Fragment F-III (/dcl I region) was sequenced from the EcoR1 site to the Bgl II site and an open reading frame found (FIG. 1). This (incomplete) sequence shows homology to known NADPH-dependent dehydrogenases from both prokaryotes and eukaryotes, such as rat corticoid 11β-dehydrogenase (Agaral et al, The Journal of Biological Chemistry, 264 18939–18943 (1989) and ribitol dehydrogenase of *Klebsiella aerogenes* (Dothie et al, Biochemical Journal 230 569–578 (1985).

The sequence is incomplete and from transcriptional data a 1.2 kb mRNA has been assigned the CAD open-reading frame, ie the DNA sequence is approximately 80 bp short.

4.4 Identification of CAD Gene

The gene was identified by matching the sequence of the N-terminus of CAD obtained from *S. clavuligerus* to the sequence predicted from the open reading frame in a portion of *S. clavuligerus* chromosomal DNA which had been cloned on a vector (see 4.2 above).

The incomplete gene sequence gives a predicted protein size of at least 32 kD. This may reflect post-translational processing of a larger precursor to give the observed protein. Alternatively, and more probably, the unsequenced portion of the genemay be small, and thus the discrepancy between genetic and biochemical estimates of protein mass may be an artefact of the SDS-PAGE conditions.

Conclusion

The results show that CAD is a 28 kD protein (by SDS-PAGE) and is encoded by the dehydrogenase-like open reading frame contained wholly within pBROC41 and pWOR14.

---

What is claimed is:

1. An isolated 4.9 kb DNA encoding a protein with clavulanic acid dehydrogenase (CAD) activity and having the endonuclease restriction pattern shown in fragment F-(IV) in FIG. 2 wherein the protein encoding sequence in the region bounded by EcoRI and BglII restriction sites is as shown in SEQ ID NO: 2.

2. An isolated DNA according to claim 1 which is derived from *Streptomyces clavuligerus* ATCC 27064.

3. A vector comprising the DNA of claim 1.

4. A microorganism transformed with the vector of claim 3.

5. A microorganism having a high copy number of the vector of claim 3.

* * * * *

Disclaimer

6,692,950 B1 — Elson et al., Madrid (ES). CLAVULANIC ACID DEHYDROGENASE, PREPARATION AND USE FOR THE PRODUCTION OF CLAVULANIC ACID. Patent dated Feb. 17, 2004, Disclaimer filed Sep. 4, 2004, by the Assignee, SmithKline Beecham P.L.C.

This patent is subject to a terminal disclaimer.

(*Official Gazette June 14, 2005*)

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 238 amino acids
      (B) TYPE: amino acid
      (C) STRANDEDNESS: unknown (D) TOPOLOGY: unknown (ii) MOLECULE TYPE: protein (iii) HYPOTHETICAL: YES (iii) ANTI-SENSE: NO (v) FRAGMENT TYPE: N-terminal (vi) ORIGINAL SOURCE:
         (A) ORGANISM: Streptomyces
         (B) STRAIN: Streptomyces clavuligerus ATCC 27064

(xi) SEQUENCE DESCRIPTION: SEQ ID NO: 1:

```
Pro Ser Ala Leu Gln Gly Lys Val Ala Leu Ile Thr Gly Ala Ser Ser
1               5                   10                  15

Gly Ile Gly Glu Ala Thr Ala Arg Ala Leu Ala Ala Glu Gly Ala Ala
            20                  25                  30

Val Ala Ile Ala Ala Arg Arg Val Glu Lys Leu Arg Ala Leu Gly Asp
        35                  40                  45

Glu Leu Thr Ala Ala Gly Ala Lys Val His Val Leu Glu Leu Asp Val
    50                  55                  60

Ala Asp Arg Gln Gly Val Asp Ala Ala Val Ser Thr Val Glu Ala
65              70                  75                  80

Leu Gly Gly Leu Asp Ile Leu Val Asn Asn Ala Gly Ile Met Leu Leu
                85                  90                  95

Gly Pro Val Glu Asp Ala Asp Thr Thr Asp Trp Thr Arg Met Ile Asp
            100                 105                 110

Thr Asn Leu Leu Gly Leu Met Tyr Met Thr Arg Ala Ala Leu Pro His
        115                 120                 125

Leu Leu Arg Ser Lys Gly Thr Val Val Gln Met Ser Ser Ile Ala Gly
    130                 135                 140

Arg Val Asn Val Arg Asn Ala Ala Val Tyr Gln Ala Thr Lys Phe Gly
145                 150                 155                 160

Val Asn Ala Phe Ser Glu Thr Leu Arg Gln Glu Val Thr Glu Arg Gly
                165                 170                 175

Val Arg Val Val Val Ile Glu Pro Gly Thr Thr Asp Thr Glu Leu Arg
            180                 185                 190

Gly His Ile Thr His Thr Ala Thr Lys Glu Met Tyr Glu Gln Arg Ile
        195                 200                 205

Ser Gln Ile Arg Lys Leu Gln Ala Gln Asp Ile Ala Glu Ala Val Arg
    210                 215                 220

Tyr Ala Val Thr Ala Pro His His Ala Thr Val His Glu Ile
225                 230                 235
```

(2) INFORMATION FOR SEQ ID NO: 2:

(i) SEQUENCE CHARACTERISTICS:
        (A) LENGTH: 1020 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
         (A) ORGANISM: Streptomyces
         (B) STRAIN: Streptomyces clavuligerus ATCC 27064

(xi) SEQUENCE DESCRIPTION: SEQ ID NO: 2:

```
AGAGGATCCC CGGGTACCGA GCTCGAATTC ACCGGGGAAT GCGACGCTGA TGATAGCGTC        60

TGCCGTGGAC GGGGAGAACT CCGGCCGCTG ATTCCCGGTG AATCCCCGGG TGTCCTCCGA       120

AGACCATCGG AGAGCGCCGC GGTATTCACC ATTCCCCGGA ACTCCCCGGG GAACTGCGGC       180

CATCCGTACC CGGTCGGCCG TGCCCACCGC AACGGTCCGG CGTACGGAAC CCGCCCCGGC       240

ACGGCAGGTC TCACCCCTTC TTCATACGCT CACCACGATC GCAGCACCAT GTGGAGGAAA       300

TGATGCCATC CGCACTCCAG GGGAAAGTCG CGCTCATCAC GGGCGCGAGC TCGGGCATCG       360

GCGAGGCCAC GGCCCGCGCC CTGGCCGCCG AGGGCGCCGC CGTGGCCATC GCCGCGCGCC       420

GGGTCGAGAA GCTGCGCGCC CTGGGTGACG AGCTGACCGC CGCCGGGGCG AAGGTCCATG       480

TCCTCGAACT CGACGTCGCC GACCGGCAGG GGGTGGACGC CGCCGTCGCC TCCACCGTCG       540

AGGCGCTGGG CGGCCTCGAC ATCCTCGTCA ACAACGCCGG GATCATGCTG CTCGGCCCGG       600

TGGAGGACGC CGACACCACC GACTGGACCC GGATGATCGA CACCAATCTC CTGGGCCTGA       660

TGTACATGAC CCGGGCGGCC CTTCCCCATC TGCTGCGCAG CAAGGGCACC GTGGTGCAGA       720

TGTCCTCGAT CGCGGGCCGG GTGAACGTCC GCAACGCGGC CGTCTACCAG GCCACGAAGT       780

TCGGTGTGAA CGCGTTCAGC GAGACGCTGC GCCAGGAGGT CACCGAGCGC GGGGTGCGGG       840

TCGTCGTCAT CGAGCCGGGC ACCACCGACA CGGAGCTGCG CGGCCACATC ACCCACACCG       900

CCACCAAGGA GATGTACGAG CAGCGGATCA GCCAGATCCG CAAGCTCCAG GCCCAGGACA       960

TCGCGGAGGC GGTCCGCTAC GCCGTGACCG CGCCGCACCA CGCGACCGTC CACGAGATCT      1020
```